United States Patent [19]

Barger, deceased et al.

[11] Patent Number: 4,464,179

[45] Date of Patent: Aug. 7, 1984

[54] MEDICAL FLUSHING VALVE

[75] Inventors: Larry N. Barger, deceased, late of Glendale, Calif.; by William A. Barger, administrator, Garfield, Kans.; Kenneth R. McCord, Menlo Park, Calif.

[73] Assignee: American Hospital Supply Corporation, Evanston, Ill.

[21] Appl. No.: 437,247

[22] Filed: Nov. 26, 1982

Related U.S. Application Data

[60] Continuation-in-part of Ser. No. 245,580, Mar. 20, 1981, Pat. No. 4,381,591, which is a division of Ser. No. 32,832, Apr. 24, 1979, Pat. No. 4,267,835.

[51] Int. Cl.³ .............................................. A61M 5/00
[52] U.S. Cl. ..................................................... 604/250
[58] Field of Search ................. 604/250, 245, 246, 30, 604/34; 251/4, 117

[56] References Cited

U.S. PATENT DOCUMENTS

| 2,706,101 | 4/1955 | Cantor | 251/4 |
| 3,675,891 | 7/1972 | Reynolds et al. | 251/117 |
| 3,934,576 | 1/1976 | Danielsson | 604/34 X |
| 4,034,754 | 7/1977 | Virag | 604/34 X |
| 4,106,675 | 8/1978 | Taylor | 604/250 |

FOREIGN PATENT DOCUMENTS 182656  3/1922  United Kingdom ............... 251/4 X Primary Examiner—John D. Yasko
Attorney, Agent, or Firm—Roger A. Williams

[57] ABSTRACT

A valve for an arterial monitoring set which continuously supplies a small flow of parenteral liquid, such as normal saline, into a patient's artery while arterial pressure is being continuously monitored. The valve has a flow restrictor providing a normally slow continuous flow rate and an elastically distortable tube which is manually squeezable to provide a fast flush rate. The valve is convenient for one hand operation.

15 Claims, 5 Drawing Figures

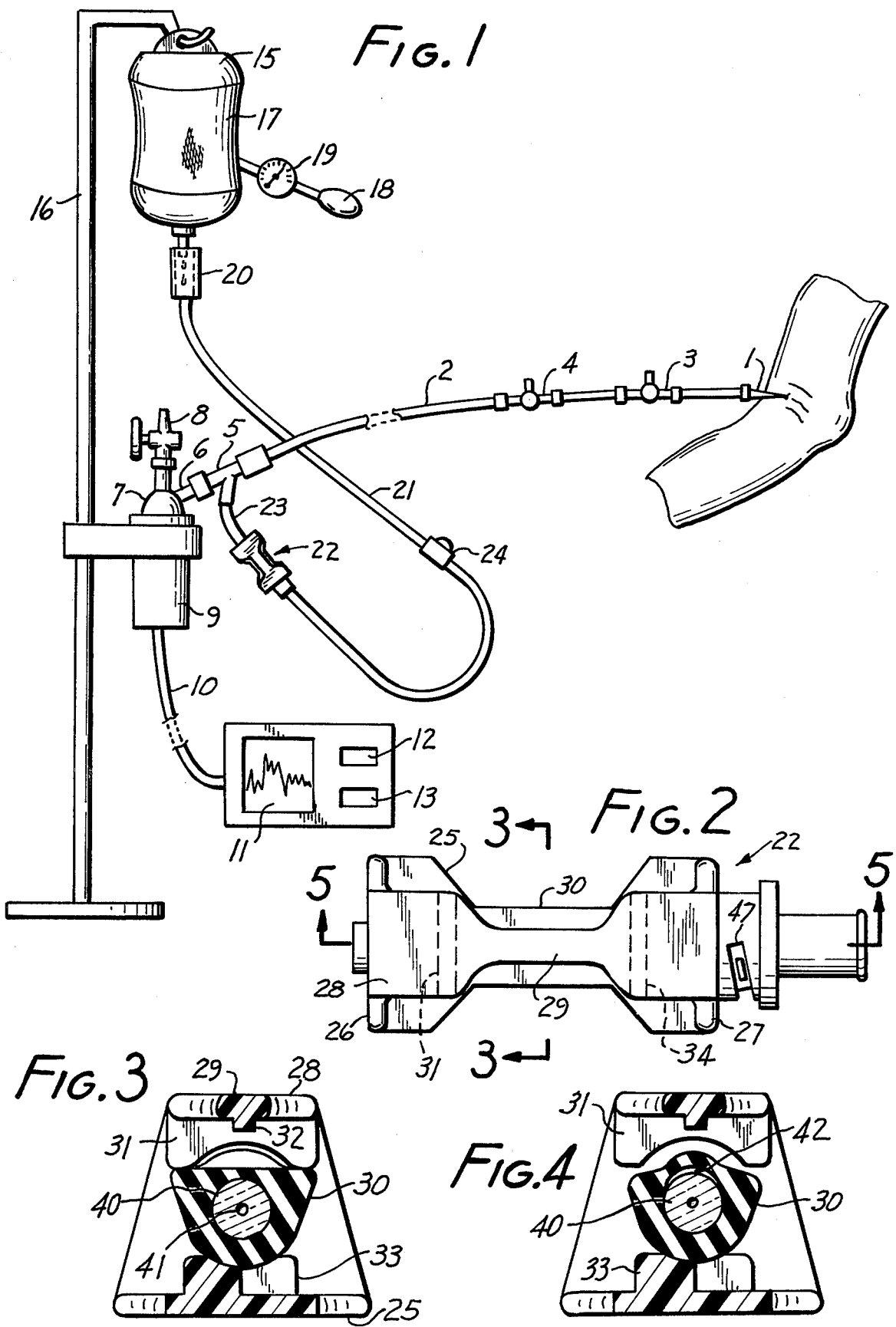

MEDICAL FLUSHING VALVE

CROSS-REFERENCE TO RELATED APPLICATIONS

This application is a continuation-in-part of U.S. Pat. application Ser. No. 245,580, filed Mar. 20, 1981, now U.S. Pat. No. 4,381,591 which application is a division of U.S. Ser. No. 032,832, filed on Apr. 24, 1979 and which issued on May 19, 1981 as U.S. Pat. No. 4,267,835.

BACKGROUND OF THE INVENTION

U.S. Pat. No. 3,581,733 describes a system for continuously monitoring blood pressure within blood vessels and the heart. The system includes a catheter joined to a connecting tube leading to a pressure transducer that converts physical pressure signals into an electrical impulse which is then fed to a recording machine, such as an oscilloscope. As pressure readings can be seriously affected if blood should coagulate in any part of the pressure monitoring system, this patent describes continuously forcing a very slow flow of a physiological salt solution (normal saline would be an example) into the patient. This very slow flow rate is sufficient to prevent blood from backing up into the catheter and connecting tube, but is so slow that it does not cause any significant error in blood pressure reading.

Immediately after connecting the system to the patient and periodically through pressure monitoring, it becomes necessary to flush a larger amount of parenteral liquid into the patient, particularly to insure that the catheter or needle is completely free of blood. U.S. Pat. No. 3,581,733 does this flushing by a valve 18. Another type flushing valve is described in Pat. No. 3,675,891. The flushing valve therein has an elongated stem that must be pulled to actuate the valve. If the valve is not physically anchored to a rigid IV pole, transducer, etc., this operation requires two hands; i.e., one to hold the valve and one to pull the stem. Should the stem ever break off during the pulling action, the valve would be rendered useless. In addition, the valve of U.S. Pat. No. 3,675,891 includes a very large number of complicated parts including special sealing gaskets, etc.

SUMMARY OF THE INVENTION

The present invention overcomes the problems described above and provides a flushing valve with a restrictor in an elastically distortable tube. The resistor combines with the tube to form a slow flow rate passage and the tube is distortable, such as by squeezing, to temporarily form a flush passage with a much faster flow rate. The body of the flushing valve includes elements for preventing rotation of the resilient distortable tube as it is distorted to actuate the valve.

BRIEF DESCRIPTION OF THE DRAWINGS

FIG. 1 is an elevational view of a blood presure monitoring system which includes the medical flushing valve;

FIG. 2 is an enlarged view of the flushing valve;

FIG. 3 is a sectional view taken along line 3—3 of FIG. 2 showing the valve in its unsqueezed condition or its normal slow flow rate;

FIG. 4 is a view similar to FIG. 3, but showing the valve squeezed into its temporary fast flush condition.

DETAILED DESCRIPTION

Figure 5:
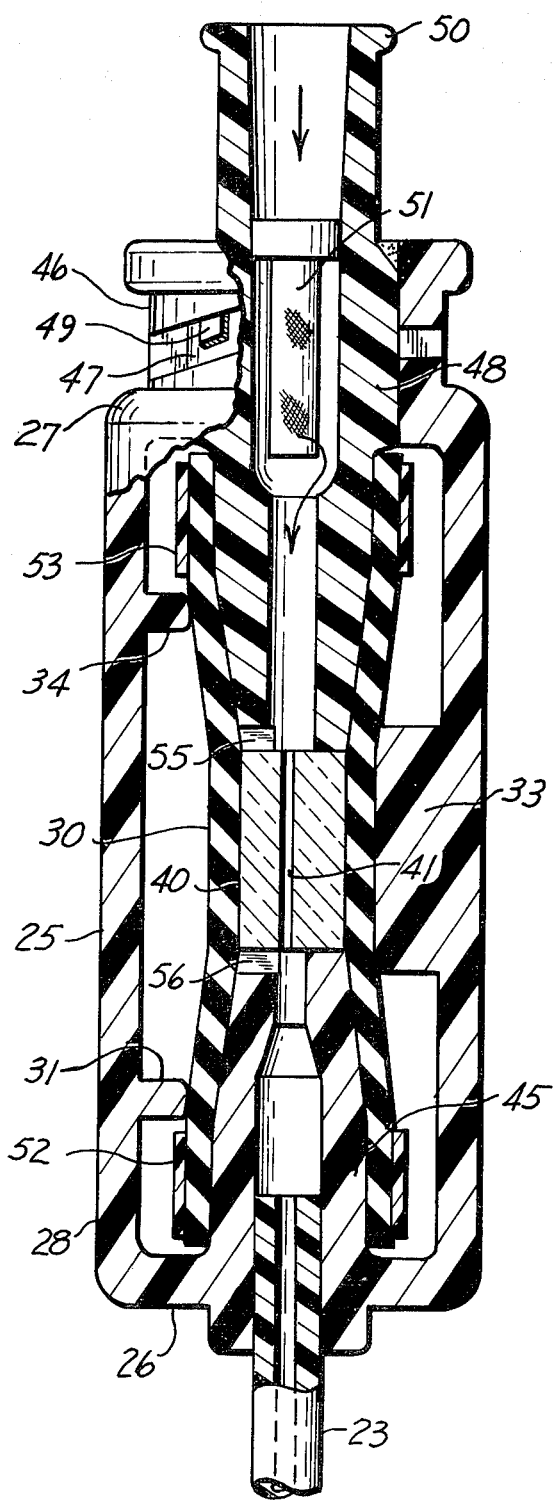
FIG. 5 is an enlarged view, partially in section, taken along line 5—5 of FIG. 2.

In FIG. 1, a system is shown for continuously monitoring blood pressure. This system has a hollow member 1, such as a needle or catheter, inserted into a patient's vein or artery. Usually blood pressure is continuously monitored from an artery because this gives a more accurate and dynamic reading of the heart function. Hydraulic pressure from the patient's artery is transmitted through a connecting tube 2 which can have ports or stopcocks, such as 3 and 4, for bleeding off blood samples or injecting medication into the patient. Tube 2 connects to a rigid T-connector 5 which is shown attached to a rigid arm 6 of a transducer pressure dome 7. It is understood that the term T-connector is used in its broad sense to also include an angled Y-connector. The transducer dome 7 includes a bleed valve 8 for use in eliminating all air from the system prior to use. It is important that no air bubbles be in the system because this can affect the hydraulic liquid pressure wave generated by the patient's heartbeat.

The pressure dome 7 of the transducer can include a diaphragm (not shown) which can respond to liquid pressure vibrations and engage electrical means inside a transducer body 9 to convert hydraulic liquid pressure surges into electrical impulses. Such electrical impulses are fed through a line 10 to an instrument 11 for reading the pressure fluctuations in a patient's cardiovascular system. Instrument 11 can be an oscilloscope, an electronically activated stylus, etc. If desired, the instrument 11 can have other monitoring functions, such as at 12 and 13, to monitor pulse rate, etc. in addition to blood pressure fluctuations at each heartbeat.

As explained above, the blood pressure monitoring for each heartbeat involves a liquid filled line between the patient and a diaphragm in the transducer dome. Since there is no liquid flow across the diaphragm of the transducer, there is no continuous blood flow out of the patient. This is why in U.S. Pat. No.3,581,733 it is necessary to very slowly force a small volume of parenteral liquid, such as normal saline, into the patient to prevent blood from backing up into the catheter and connecting tube 2 where it could coagulate over an extended period of time. Coagulated blood portions in the system can materially affect the accuracy of a pressure monitoring because such coagulated blood forms a restriction in the hydraulic pressure system. This very slow infusion of parenteral liquid (such as at 3 cc/hour) into the patient is from a container 15 supported on a pole structure 16. Preferably, container 15 is of the collapsible bag type with a pressure cuff 17 that includes a squeeze bulb 18 and pressure gauge 19. The parenteral liquid flows from container 15 through a drip chamber 20 and a connecting tube 21 to a valve shown generally at 22 which is joined by flexible tube segment 23 to the rigid T-connector 5. Flow through connecting tube 21 can be controlled by conventional roller clamp 24.

The structure of the valve shown generally at 22 is the subject matter of the present invention. Related co-owned patents filed on the same day as the parent application of the present application are "Method of Flushing A Medical Liquid," U.S. Pat. No. 4,267,833; "System For Flushing A Medical Liquid," U.S. Pat.

No. 4,267,834; "Medical Flushing Valve," U.S. Pat. No. 4,267,835; and "Protector Housing For Squeezable Valve" (Design), filed Apr. 24, 1979, Ser. No. 32,971. The entire disclosures of each of the above related patents are incorporated herein by this reference.

In FIG. 2, the enlarged view of the valve illustrates a protector housing that includes a base 25 connected to ends 26 and 27, which in turn are connected to a top 28 that has a narrow central section 29. Within the protector housing is an elastically distortable squeeze tube of rubber-like material, such as silicone. Preferably, this squeeze tube 30 is generally transparent, or at least translucent to aid in detecting any air bubbles in the valve.

As shown in FIG. 3, the top wall has a longitudinal bracing rib 32 which extends through its longitudinal length to strengthen narrow portion 29 of the top. Bottom wall 25 has a limit lug such as cradle 33, with a concave surface, for preventing excess distortion of squeeze tube 30. Preferably, squeeze tube 30 has a generally triangular cross-sectional shape.

In FIG. 3, the valve is shown in its normal continuous slow flow rate position with the squeeze tube 30 sealingly engaging the periphery of a fixed size rigid glass flow restrictor 40 that has a bore 41 with a diameter of 0.001 to 0.004 inch. A diameter of 0.002 inch works very well and the restrictor can be made of glass tubing, such as is used for glass thermometers.

When it becomes necessary to fast flush the system of FIG. 1 with the parenteral liquid, the elastically distortable tube 30 is manually pinched through side openings of the protector housing. This causes the tube 30 to temporarily distort and create a flushing passage 42 around restrictor 40. When this is done, cradle 33 and cradles 31 and 34 prevent rotation and/or undue flexure of the distortable squeeze tube which might dislocate the restrictor. Release of the squeeze tube 30 causes it to immediately resume the FIG. 3 configuration and the predetermined slow flow rate is resumed.

The valve structure includes a cradle 31 and cradle 34 attached to the top 28. The cradles 31 and 34 cooperate with the distortable squeeze tube 30 to prevent rotation of the distortable squeeze tube. It is desirable to prevent rotation of the distortable squeeze tube in order to facilitate creation of the bypass flushing passage 42 around the restrictor 40 upon application of an external force to the distortable squeeze tube. The cradles 31 and 34 also cooperate with the cradle 33 for preventing unnecessary rotation of the distortable squeeze tube which could bring about slippage of the squeeze tube from its stationary hollow connector 45 or the movable connector 48. As can be seen in FIGS. 3 and 4, the cradle 31 can be somewhat concave in shape with projecting ears which extend around the distortable squeeze tube which itself extends around the hollow connector 45.

Perhaps the valve structure can best be understood by referring to the enlarged sectional view in FIG. 5. Here the housing's end wall 26 is integrally formed with a stationary hollow connector 45 which is joined to flexible tube segment 23. End wall 27 of the protector housing is joined to a tubular retainer 46 that has a bayonet type locking channel 47. This bayonet type lock can also be seen in FIG. 2. Fitting within tubular retainer 46 is a longitudinally movable hollow connector 48 which has a bayonet type lug 49 which engages slow 47 of retainer 46. Movable connector 48 has an internally tapered outer end and retaining ears 50 for connecting with connecting tube 21 leading from the parenteral liquid source.

As liquid is delivered from the pressurized parenteral liquid source in the system shown in FIG. 1, it flows to the left as shown by the flow arrows in FIG. 5. The liquid enters a hollow filter assembly 51 that is inside connector 48. After the liquid exits through sides of the filter as shown by the arrow, it travels to the flow restrictor 40 and the pressure forces the liquid through the restricted passage 41. The elastic tube 30 tightly seals against the external periphery of glass tube 40 and prevents any other passage of liquid other than through restricted passage 41. To firmly hold ends of the tube 30 in place, compression shrink bands 52 and 53 can be used, if desired.

When it is desired to fast flush the system of FIG. 1, the elastically distortable tube 30 is laterally squeezed between thumb and forefinger causing an upper portion of tube 30 to lift off the periphery of glass tube 40 creating a flush passage. Thus, the liquid can flow thorugh lateral passage 55 of connector 48, and go around restrictor 40 and enter the passage of connector 45 through its lateral passage 56.

It is important that air bubbles be eliminated from the system as they can interfere with the hydraulic pressure waves being transmitted from the patient to the transducer. For this reason, it is important that the hollow connectors 45 and 48 abuttingly engage ends of the restrictor 40 so no undue pockets are formed which could trap air bubbles.

It has been found that the flushing valve of the present invention works very well when the flow restrictor is of glass, the squeeze tube is of silicone rubber, and the protective housing and hollow adapters are made of a rigid thermoplastic material.

In the above description, a specific example has been used to illustrate the invention. However, it is understood by those skilled in the art that certain modifications can be made to this example without departing from the spirit and scope of the invention.

We claim:

1. A medical flushing valve comprising:
   an elastically distortable tube with a noncircular outer surface that includes a force concentrating section;
   a protector housing extending around the elastically distortable tube;
   means on the protector housing for preventing rotation of the elastically distortable tube; and
   a restrictor in the tube which combines with the tube to form a restricted passage means in the form of a fixed size bore extending through the restrictor and having a predetermined flow rate therethrough, said tube being distortable by application of a force to such force concentrating section of the outer surface of the tube to temporarily form a flush passage in the valve having a substantially faster flow rate during the application of such force, which tube is adapted to close the flush passage upon removal of such force from the force concentrating section.

2. A medical flushing valve as set forth in claim 1 wherein the tube separates from the restrictor to form the flush passage.

3. A medical flushing valve as set forth in claim 1 wherein the tube has end portions that extend beyond ends of the restrictor, and a hollow connector is joined to each end portion.

4. A medical flushing valve as set forth in claim 3 wherein the connectors abuttingly seal against ends of the restrictor and the connectors have lateral port means for communicating with the flush passage.

5. A medical flushing valve as set forth in claim 4 wherein at least one connector is longitudinally movable relative to the protector housing.

6. A medical flushing valve as set forth in claim 1 wherein the tube is laterally compressible to form the flush passage.

7. A medical flushing valve as set forth in claim 6 wherein the tube has a generally triangular cross section with at least one of the triangular corners of the tube providing the force concentrating section of the tube's outer surface.

8. A medical flushing valve as set forth in claim 1 wherein the protector housing has a base extending between the two connectors and the base has an upstanding limit lug for engaging the tube when laterally squeezed to prevent undue displacement of the tube.

9. A medical flushing valve as set forth in claim 1 wherein the protector housing has a base extending between the two connectors and a top portion extending between the two connectors.

10. A medical flushing valve as set forth in claim 9 wherein the means for preventing rotation of the tube comprises at least one cradle structure attached to the top of the protector housing which cooperates with the tube to prevent rotation of the tube.

11. A medical flushing valve as set forth in claim 1 further comprising means for holding the end of the distortable tube in fluid sealing contact with the hollow connectors.

12. A medical flushing valve comprising:
an elastically distortable tube with a noncircular outer surface that includes a force concentrating section;
a protector housing extending around the distortable tube;
means on the protector housing for preventing rotation of the distortable tube relative to the protector housing; and
a rigid restrictor block having a fixed size bore and which restrictor block is sealingly secured in the tube, said tube being distortable by application of a force to such force concentrating section of the tube's outer surface for separating the tube from the block to temporarily form a flush passage between the block and tube, which flush passage has a substantially greater flow rate than the bore of the block during the application of such force, and which tube is adapted to close the flush passage upon removal of such force form the force concentrating section.

13. A medical flushing valve as set forth in claim 12 wherein the means for preventing rotation of the distortable tube comprises a concave surface integral with the protector housing, which concave surface contacts the distortable tube to prevent rotation of the distortable tube.

14. A medical flushing valve comprising:
an elastically distortable tube;
a protector housing extending around the distortable tube;
means on the protector housing for preventing rotation of the distortable tube;
a restrictor in the distortable tube which has a fixed size bore having a predetermined flow rate therethrough, said tube being distortable to temporarily form a flush passage through the valve having a substantially faster flow rate than the flow rate through the bore;
said tube extending beyond ends of the restrictor;
connectors joined to end portions of the tube; and
spiral adjustment means for longitudinally moving the connectors into sealing contact with the restrictor, whereby the restrictor is compressingly held between the connectors to avoid leakage around the restrictor when the flush passage is closed.

15. A medical flushing valve as set forth in claim 14 wherein the means for preventing rotation of the distortable tube comprises at least one outward projection on the protector housing, which projection engages the distortable tube to prevent rotation of the distortable tube.

* * * * *